United States Patent
Desai et al.

(10) Patent No.: US 10,815,227 B2
(45) Date of Patent: Oct. 27, 2020

(54) PROCESSES FOR THE PREPARATION OF FILGOTINIB

(71) Applicant: CADILA HEALTHCARE LIMITED, Ahmedabad, Gujarat (IN)

(72) Inventors: Sanjay Jagdish Desai, Gujarat (IN); Kuldeep Natwarlal Jain, Gujarat (IN); Naitik Bharatbhai Patel, Gujarat (IN); Hemant Kumar Singh, Gujarat (IN)

(73) Assignee: CADILA HEALTHCARE LIMITED (IN)

( * ) Notice: Subject to any disclaimer, the term of this patent is extended or adjusted under 35 U.S.C. 154(b) by 0 days.

(21) Appl. No.: 16/548,992

(22) Filed: Aug. 23, 2019

(65) Prior Publication Data
US 2020/0062744 A1 Feb. 27, 2020

(30) Foreign Application Priority Data
Aug. 27, 2018 (IN) .............................. 201821031972

(51) Int. Cl.
*C07D 417/10* (2006.01)
(52) U.S. Cl.
CPC .................... *C07D 417/10* (2013.01)
(58) Field of Classification Search
CPC .................................................. C07D 417/10
See application file for complete search history.

(56) References Cited

U.S. PATENT DOCUMENTS

| 8,088,764 B2 | 1/2012 | Menet et al. |
| 8,853,240 B2 | 10/2014 | Menet et al. |
| 9,382,247 B2 | 7/2016 | Sabourault et al. |
| 9,707,237 B2 | 7/2017 | Menet et al. |

FOREIGN PATENT DOCUMENTS

| CN | 104987333 B | * | 1/2017 |
| WO | 2017162139 A1 | | 9/2017 |
| WO | 2018024236 A1 | | 2/2018 |

* cited by examiner

*Primary Examiner* — Shawquia Jackson
(74) *Attorney, Agent, or Firm* — Renner Kenner Greive Bobak Taylor & Weber

(57) ABSTRACT

The present invention relates to processes for the preparation of Filgotinib. The present invention relates to novel processes for the preparation of filgotinib. The present invention also relates to novel intermediates for the preparation of filgotinib.

17 Claims, No Drawings

PROCESSES FOR THE PREPARATION OF FILGOTINIB

FIELD OF THE INVENTION

The present invention relates to processes for the preparation of Filgotinib. In particular, the present invention relates to novel processes for the preparation of filgotinib. The present invention also relates to novel intermediates used for the preparation of filgotinib.

BACKGROUND AND THE PRIOR ART

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Filgotinib is namely a JAK1 inhibitor and has code GLPG0634. Its chemical name is N-[5-[4-[1,1-dioxo-4-thiomorpholinyl] methyl] phenyl][1,2,4] triazolo [1,5-A] pyridin-2-yl]cyclopropanecarboxamide. Filgotinib is having the structure of Formula (I)

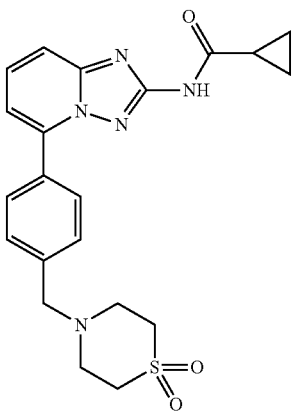

(I)

U.S. Pat. No. 8,088,764 B2 discloses the compound filgotinib and provides its process for preparation.

U.S. Pat. No. 8,853,240 B2 relates to method of treatment of arthritis with a pharmaceutical composition comprising filgotinib.

U.S. Pat. No. 9,382,247 B2 relates to crystalline form of Filgotinib hydrochloride hydrate.

U.S. Pat. No. 9,707,237 B2 relates to filgotinib maleic acid salt.

WO 2017162139 A1 discloses various crystalline forms of filgotinib hydrochloride designated as Form-A to Form-D and process preparing thereof.

WO 2018024236 A1 discloses various crystalline forms filgotinib designated as CS1 to CS3 and process for preparing thereof.

The process disclosed in prior art for preparing filgotinib involves lengthy and hazardous reaction step.

In view of the above art, there is provided new improved processes for preparing filgotinib which are eco-friendly, cost effective and commercially applicable.

SUMMARY OF THE INVENTION

In one general aspect, there is provided a process for the preparation of filgotinib of Formula (I),

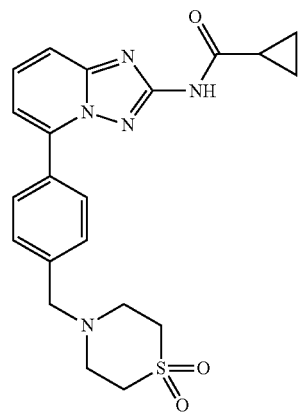

(I)

comprising the steps of:

(a) reacting a compound of Formula (II) with a compound of Formula (III) to obtain a compound of Formula (IV); and

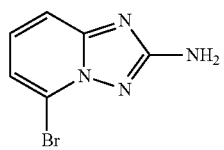

(II)

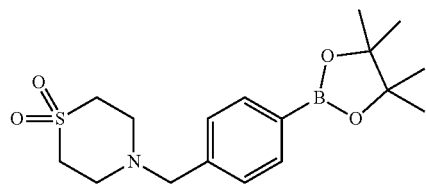

(III)

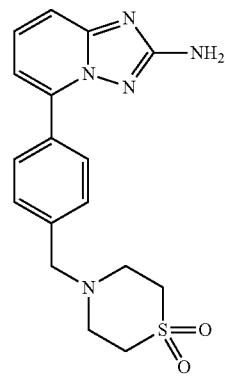

(IV)

(b) reacting compound of Formula (IV) with cyclopropanecarbonyl chloride of Formula (V) to obtain filgotinib of Formula (I).

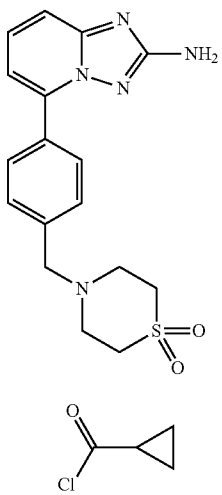

(IV)

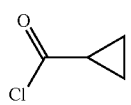

(V)

In another general aspect, there is provided a process for the preparation of filgotinib of Formula (I) comprising the steps of:

(a) reacting a compound of Formula (VI) with ethoxycarbonyl isothiocynate of Formula (VII) to obtain a compound of Formula (VIII);

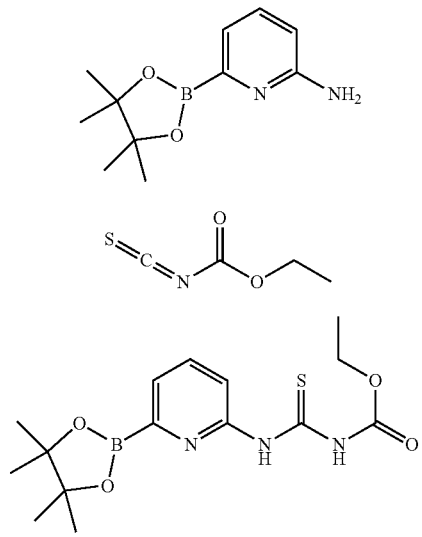

(VI), (VII), (VIII)

(b) converting compound of Formula (VIII) to a compound of Formula (IX);

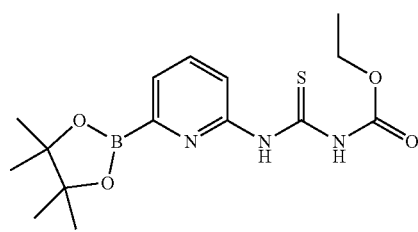

(VIII)

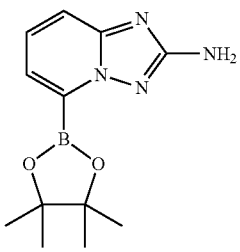

(IX)

(c) reacting a compound of Formula (IX) with cyclopropanecarbonyl chloride of Formula (V) to obtain compound of Formula (X); and

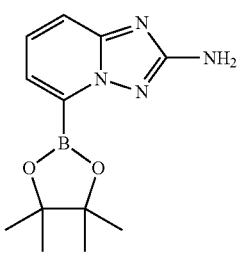

(IX)

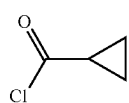

(V)

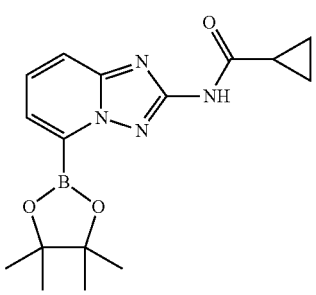

(X)

(d) reacting a compound of Formula (X) with 4-(4-bromobenzyl)thiomorpholine 1,1-dioxide of Formula (XI) to obtain filgotinib of Formula (I).

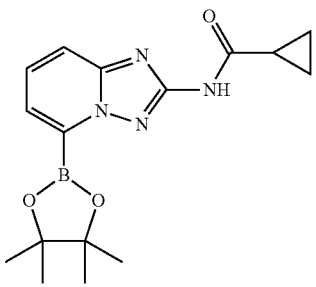

(X)

-continued

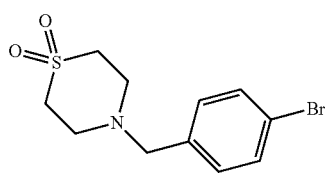
(XI)

In another general aspect, there is provided novel compounds of Formula (VIII), (IX) and (X) for preparing filgotinib of Formula (I).

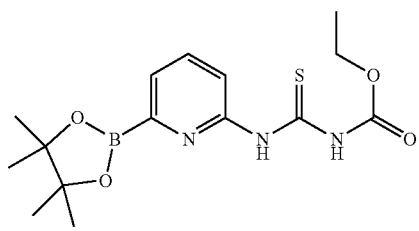
(VIII)

(IX)

(X)

In another general aspect, there is provided a process for the preparation of filgotinib of Formula (I) comprising the steps of:

(a) converting a compound of Formula (XII) to a compound of Formula (XIII);

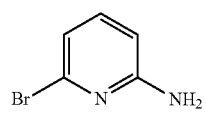
(XII)

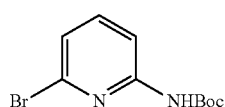
(XIII)

(b) reacting a compound of Formula (XIII) with a compound of Formula (III) to obtain a compound of Formula (XIV) or directly reacting a compound of Formula (XII) with a compound of Formula (III) to obtain a compound of Formula (XIV);

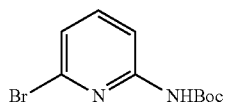
(XIII)

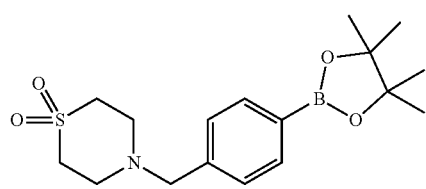
(III)

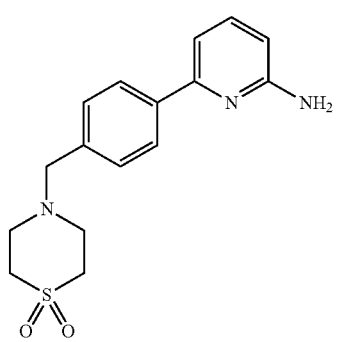
(XIV)

(c) reacting a compound of Formula (XIV) with ethoxycarbonyl isothiocynate of Formula (VII) to obtain a compound of Formula (XV);

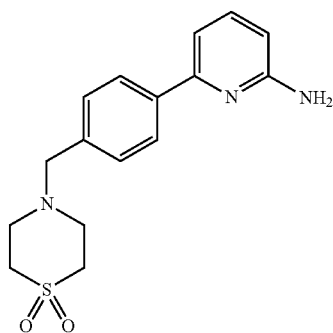
(XIV)

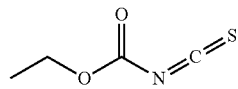
(VII)

(XV)

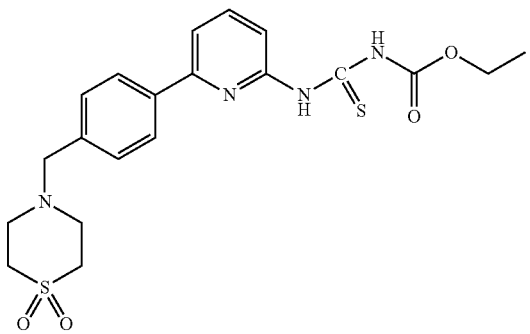

(d) converting a compound of Formula (XV) to a compound of Formula (IV); and (e) reacting compound of Formula (IV) with cyclopropanecarbonyl chloride of Formula (V) to obtain filgotinib of Formula (I).

(IV)

(V)

DETAILED DESCRIPTION OF THE INVENTION

The aforementioned objectives of the present invention are fulfilled by one or more of the processes described herein.

While the invention has been described in terms of its specific embodiments, the description, in no way, intends to limit the scope of the present invention to the specifically described embodiments only; equivalents and variants thereof which are apparently obvious to those skilled in the art are also included within the scope of the present invention. The description does not include detailed description of conventional methods used in the field of the invention; such conventional methods are the ones well known to those of ordinary skill in the art either because they are normally practiced routinely by the skilled artisan in the field of the invention and/or are described in detail in various publications—physical as well digital.

The terms 'reacting', 'contacting' and 'treating' are generally interchangeable and are used in their ordinary meaning as they are used in the field of the invention, unless defined specifically otherwise.

The term 'converting' means reacting the compound to which it refers to with another compound and/or reagent; and/or subjecting it to condition(s) wherein it transforms to another compound as a result of such treatment.

The terms 'isolating', 'obtaining' and 'purifying' are generally interchangeable and include, but not limited to, decantation, filtration, extraction, evaporation, crystallization, recrystallization and chromatographic operations.

The expressions that recite a range of values "between" two values include the endpoints. Terms such as "about" and "generally" are to be construed as modifying a term or value to which they are attached such that the term or the value is not absolute. This includes, at very least, the degree of expected experimental error, technique error and instrument error for a given technique used to measure a value.

The product(s) obtained may further be purified to obtain them in purer form.

The product(s) obtained may further be dried additionally to achieve desired level of moisture and/or residual solvents.

The product(s) obtained may further be converted to any other physical forms thereof which includes but not specifically limited to polymorph(s), salt(s), solvate(s), hydrate(s), co-crystal(s) or solid dispersion(s); and crystalline or amorphous forms thereof.

The product(s) obtained may further be subjected to physical processing which includes, but not limited to, pressing, crushing, triturating, milling or grinding to adjust the particle size of the product(s) to desired levels.

The product(s) obtained may further be combined with pharmaceutically acceptable career to obtain a pharmaceutical composition comprising filgotinib of the invention and pharmaceutically acceptable carriers, excipients or diluents. The pharmaceutical composition may be in the form of solid or liquid dosage forms and may have immediate release or modified release characteristics. The dosage forms include but not limited to tablet, capsule, powder, granules, solution, suspension, emulsion, elixir or cream.

In one general aspect, there is provided a process for the preparation of filgotinib of Formula (I), (I)

comprising the steps of:

(a) reacting a compound of Formula (II) with a compound of Formula (III) to obtain a compound of Formula (IV); and

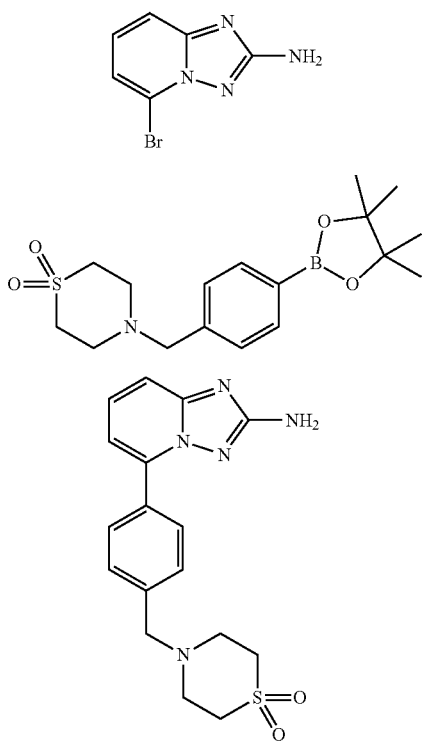

(b) reacting compound of Formula (IV) with cyclopropanecarbonyl chloride of Formula (V) to obtain filgotinib.

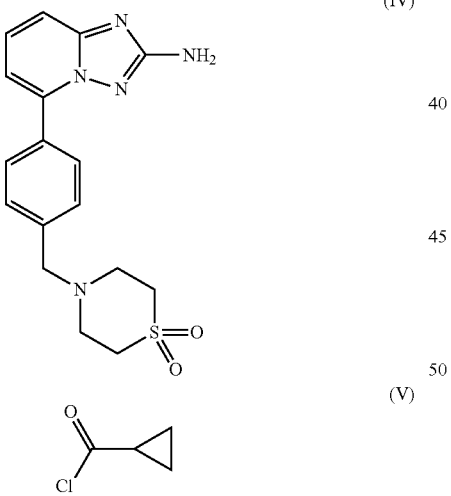

The compound of Formula (II) can be reacted with compound of Formula (III) by using a catalyst in presence of a base in one or more solvents to obtain compound of Formula (IV).

The compound of Formula (IV) can be reacted with cyclopropanecarbonyl chloride of Formula (V) in one or more solvents using a base to obtain filgotinib.

The catalyst may be selected from Palladium scavenger being used in Suzuki coupling. The catalyst may be selected from Pd(PPh$_3$)$_4$, PdCl$_2$(PPh$_3$)$_4$, PdCl$_2$(dppf) and PdCl$_2$(dppe).

The base may be selected from an organic or inorganic base. An organic base may be selected from diisopropylethylamine, diisopropylamine, triethylamine, diethylamine, piperidine, morpholine, pyridine, DBU and DABCO. The inorganic base comprises of an alkali and alkaline metal hydroxide and carbonate, in particular the suitable alkali metal hydroxide comprises of sodium hydroxide, potassium hydroxide, lithium hydroxide and carbonate comprises of sodium carbonate, potassium carbonate and cesium carbonate.

In general, the solvent comprises one or more of C$_{1-4}$ alcohols, C$_{2-6}$ esters, ketones, halogenated hydrocarbons, polar aprotic solvents, tetrahydrofuran, 2-methyltetrahydrofuran, dioxane, or mixtures thereof.

In general, the C$_{1-4}$ alcohol is selected from methanol, ethanol, n-propanol, isopropanol, and n-butanol; the C$_{2-6}$ ester is selected from ethyl acetate, propyl acetate, isopropyl acetate, t-butyl acetate, and isobutyl acetate; the ketone is selected from acetone, methyl ethyl ketone, and methyl isobutyl ketone; the halogenated hydrocarbon is selected from methylene dichloride, ethylene dichloride, carbon tetrachloride and chlorobenzene; and the polar aprotic solvent is selected from dimethylformamide, dimethylsulfoxide and N-methylpyrrolidone or mixture thereof.

In another general aspect, there is provided a process for the preparation of filgotinib of Formula (I) comprising the steps of:

(a) reacting a compound of Formula (VI) with ethoxycarbonyl isothiocynate of Formula (VII) to obtain a compound of Formula (VIII);

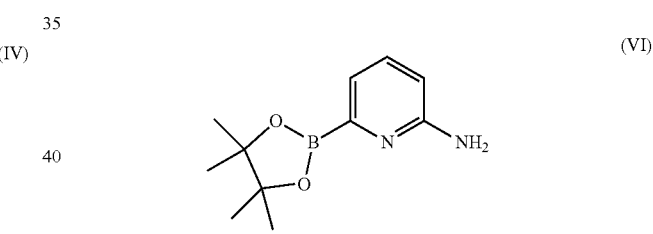

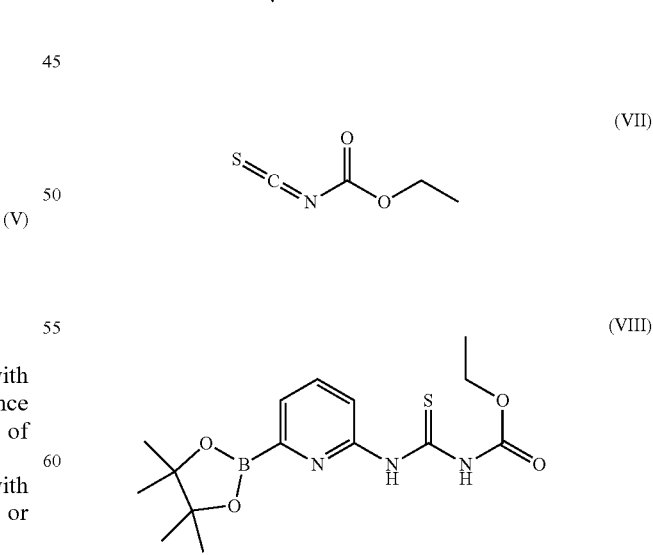

(b) converting compound of Formula (VIII) to a compound of Formula (IX);

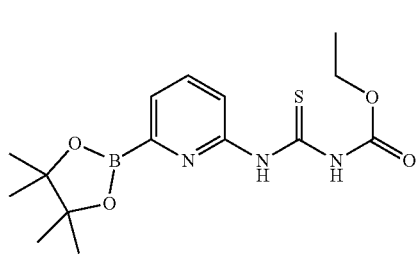
(VIII)

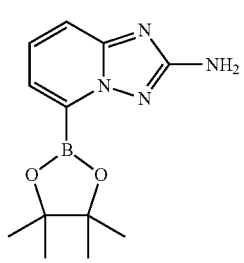
(IX)

(c) reacting a compound of Formula (IX) with cyclopropanecarbonyl chloride of Formula (V) to obtain compound of Formula (X); and

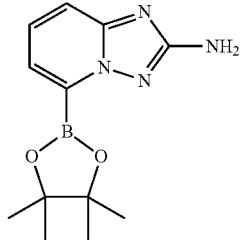
(IX)

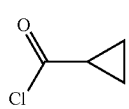
(V)

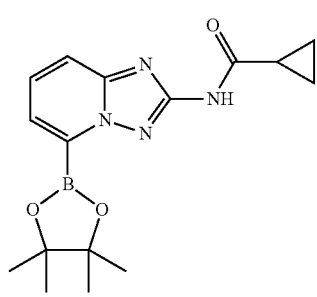
(X)

(d) reacting a compound of Formula (X) with 4-(4-bromobenzyl)thiomorpholine 1,1-dioxide of Formula (XI) to obtain filgotinib.

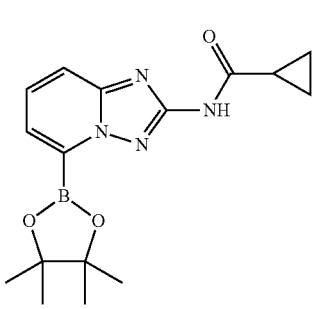
(X)

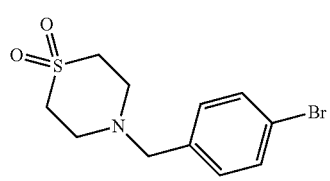
(XI)

The compound of Formula (VI) can be reacted with ethoxycarbonyl isothiocynate of Formula (VII) in one or more solvents to obtain compound of Formula (VIII).

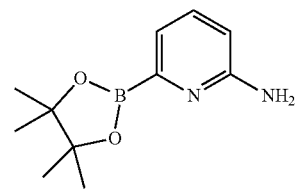
(VI)

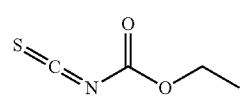
(VII)

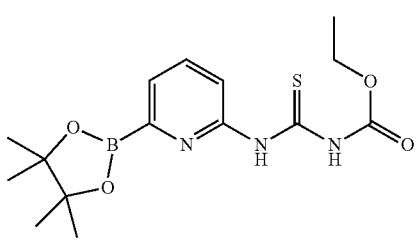
(VIII)

The compound of Formula (VIII) is converted to a compound of Formula (IX) in presence of base in one or more solvents.

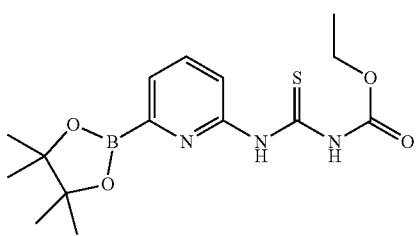
(VIII)

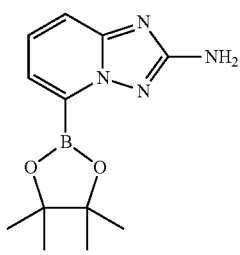

(IX)

The compound of Formula (IX) is reacted with cyclopropanecarbonyl chloride of Formula (V) in presence of base and one or more solvents to obtain compound of Formula (X).

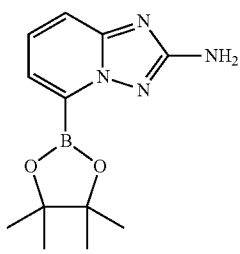

(IX)

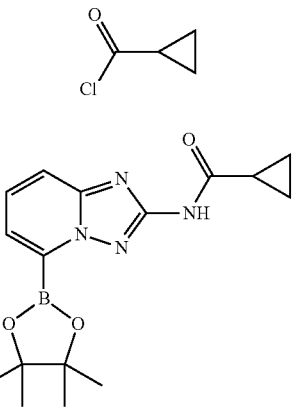

(V)

(X)

The compound of Formula (X) is reacted with 4-(4-bromobenzyl)thiomorpholine 1,1-dioxide of Formula (XI) to obtain filgotinib of Formula (I) in presence of catalyst and base in one or more solvents to obtain filgotinib.

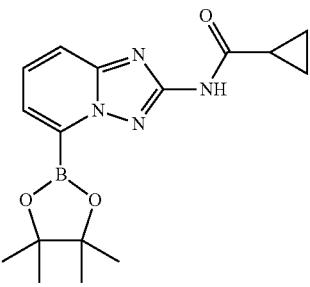

(X)

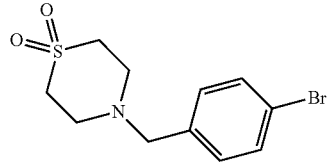

(XI)

In another general aspect, there is provided novel compound of Formula (VIII)

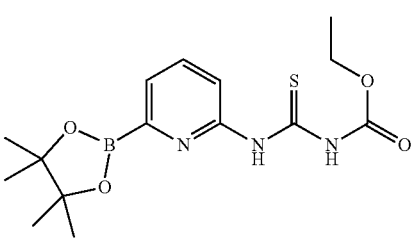

(VIII)

for preparing filgotinib of Formula (I).

In another general aspect, there is provided novel compound of Formula (IX)

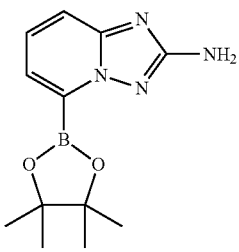

(IX)

for preparing filgotinib of Formula (I).

In another general aspect, there is provided novel compound of Formula (X)

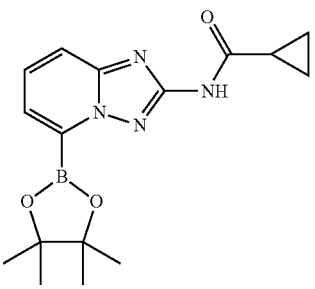

(X)

for preparing filgotinib of Formula (I).

In another general aspect, there is provided a process for the preparation of filgotinib of Formula (I) comprising the steps of:

(a) converting a compound of Formula (XII) to a compound of Formula (XIII); or

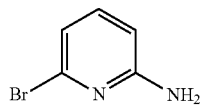
(XII)

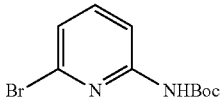
(XIII)

(a) reacting a compound of Formula (XII) with a compound of Formula (III) using a catalyst in presence of a base in one or more solvents to obtain a compound of Formula (XIV);

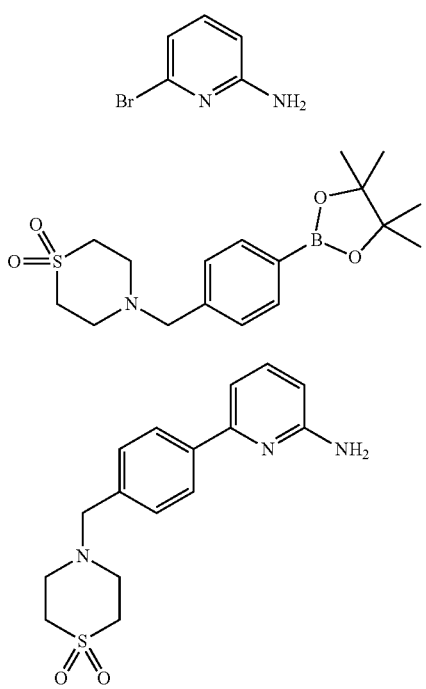

(b) reacting a compound of Formula (XIV) with ethoxycarbonyl isothiocynate of Formula (VII) in one or more solvents to obtain a compound of Formula (XV);

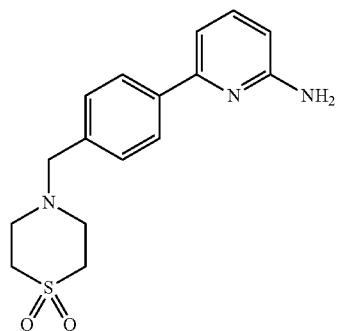
(XIV)

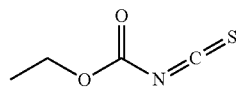
(VII)

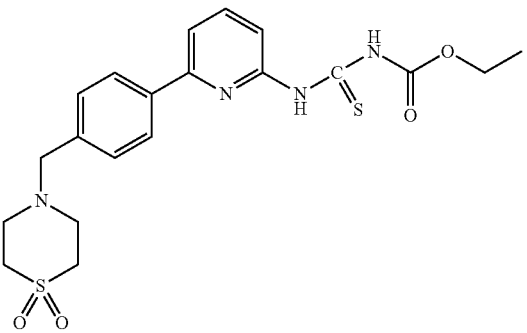
(XV)

(c) reacting a compound of Formula (XV) with a base in presence of one or more solvents to obtain a compound of Formula (IV); and

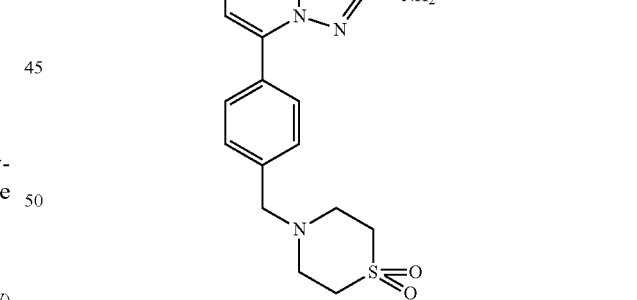

(d) reacting compound of Formula (IV) with cyclopropanecarbonyl chloride of Formula (V) in presence of base and one or more solvents to obtain filgotinib of Formula (I).

The catalyst may be selected from Palladium scavenger being used in Suzuki coupling. The catalyst may be selected from Pd(PPh$_3$)$_4$, PdCl$_2$(PPh$_3$)$_4$, PdCl$_2$(dppf) and PdCl$_2$(dppe).

The base may be selected from an organic or inorganic base. An organic base may be selected from diisopropylethylamine, diisopropylamine, triethylamine, diethylamine, piperidine, morpholine, pyridine, DBU and DABCO. The inorganic base comprises one or more of an alkali and alkaline metal hydroxide and carbonate. In particular, the suitable alkali metal hydroxide comprises one or more of sodium hydroxide, potassium hydroxide and lithium hydroxide and carbonate comprises one or more of sodium carbonate, potassium carbonate and cesium carbonate.

In general, the solvent comprises one or more of $C_{1-4}$ alcohols, $C_{2-6}$ esters, ketones, halogenated hydrocarbons, polar aprotic solvents, tetrahydrofuran, 2-methyltetrahydrofuran, dioxane, or mixtures thereof.

In general, the $C_{1-4}$ alcohol is selected from methanol, ethanol, n-propanol, isopropanol, and n-butanol; the $C_{2-6}$ ester is selected from ethyl acetate, propyl acetate, isopropyl acetate, t-butyl acetate, and isobutyl acetate; the ketone is selected from acetone, methyl ethyl ketone, and methyl isobutyl ketone; the halogenated hydrocarbon is selected from methylene dichloride, ethylene dichloride, carbon tetrachloride and chlorobenzene; and the polar aprotic solvent is selected from dimethylformamide, dimethylsulfoxide and N-methylpyrrolidone, or mixture thereof.

In another general aspect, there is provided a process for the preparation of filgotinib as depicted in Scheme-1.

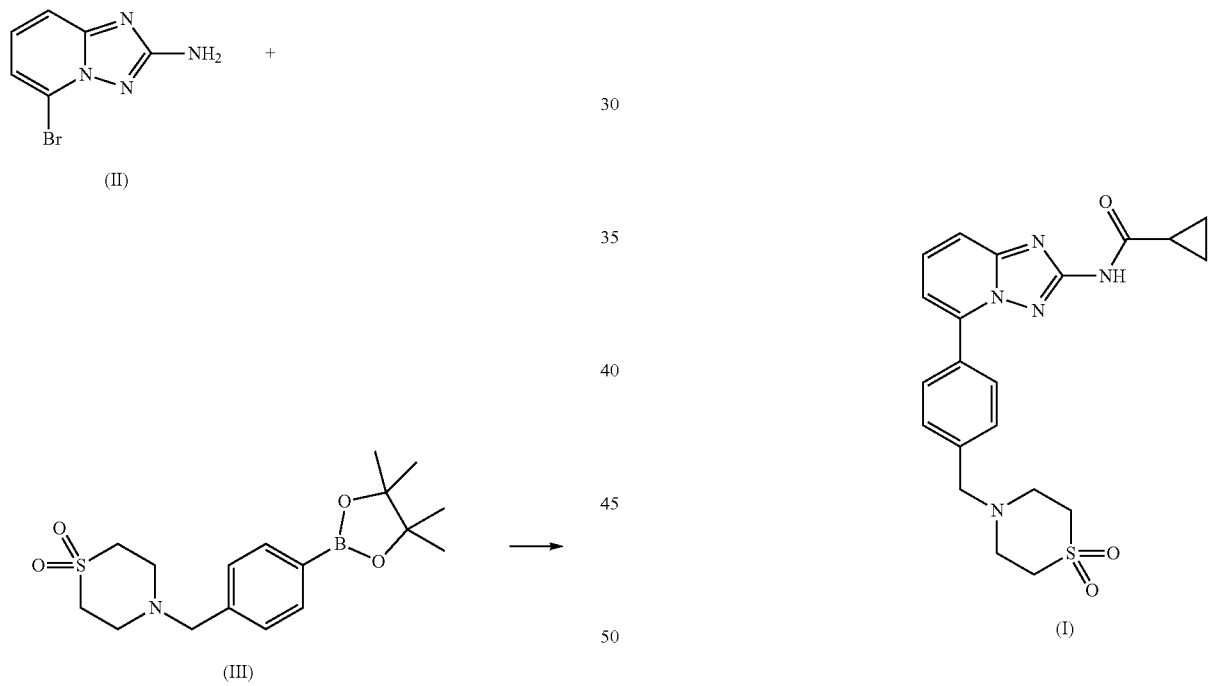

In another general aspect, there is provided a process for the preparation of filgotinib as depicted in Scheme-2.

Scheme-2

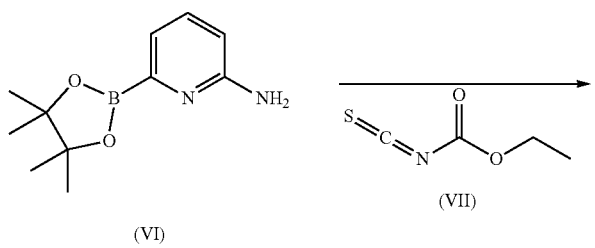

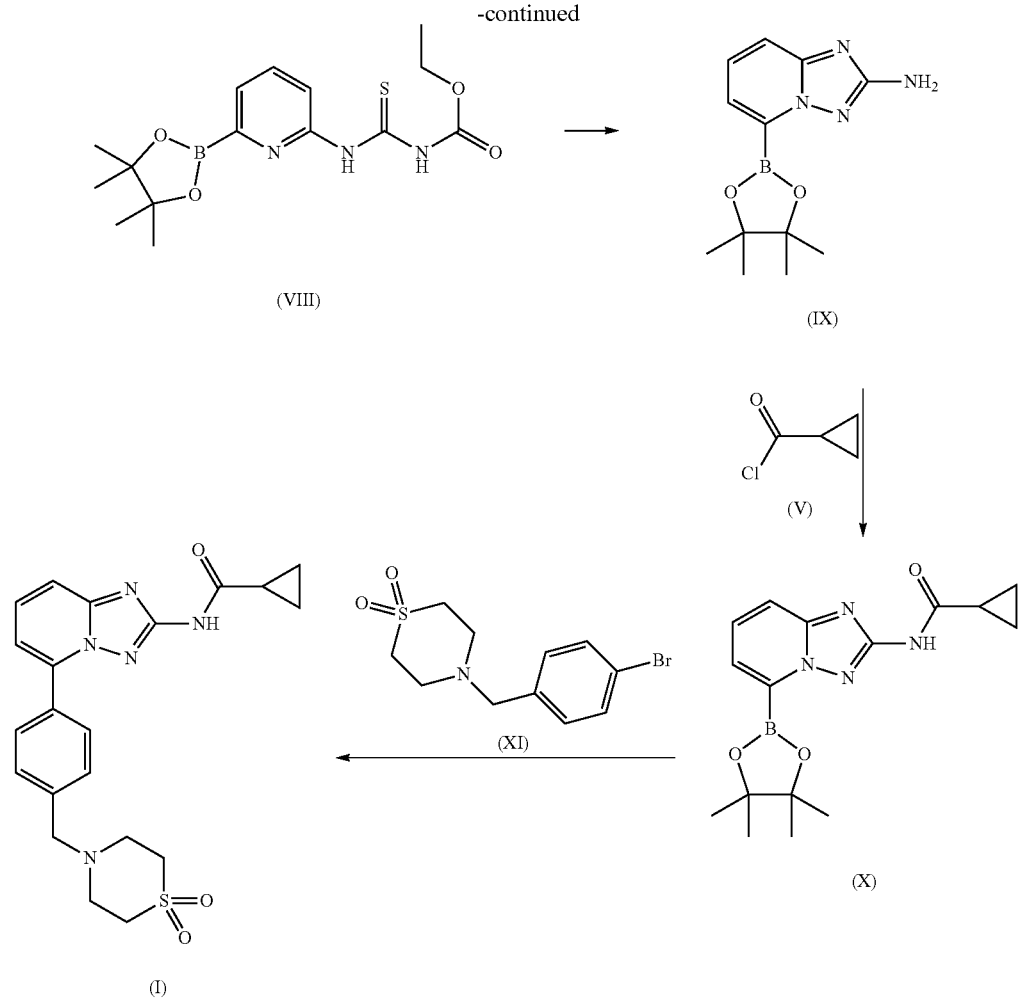
In another general aspect, there is provided a process for the preparation of filgotinib as depicted in Scheme-3.
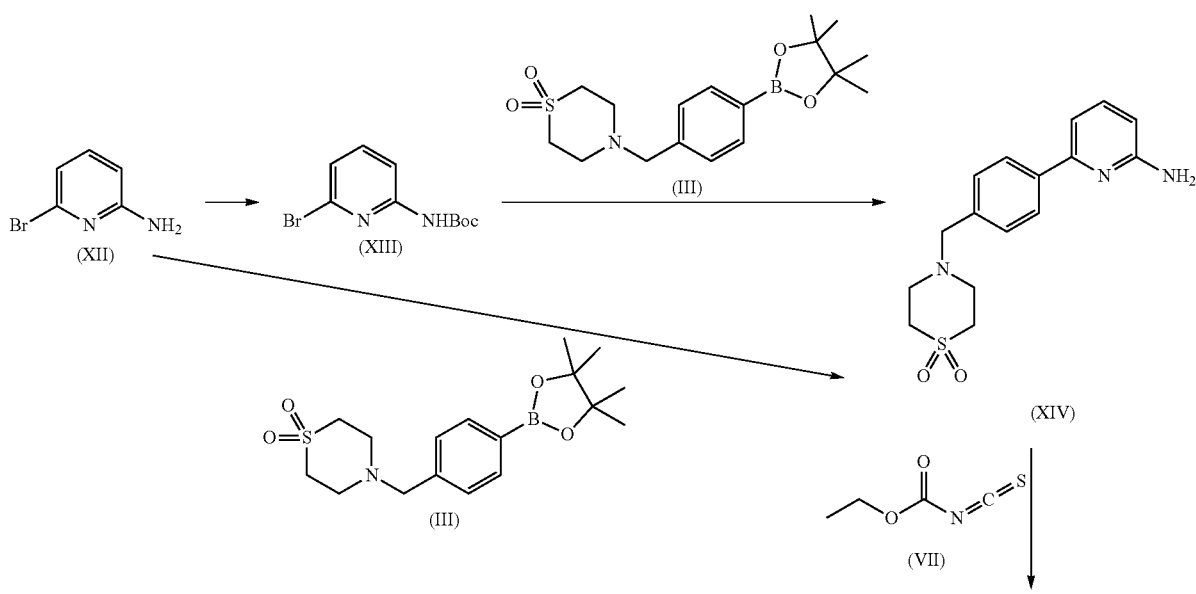

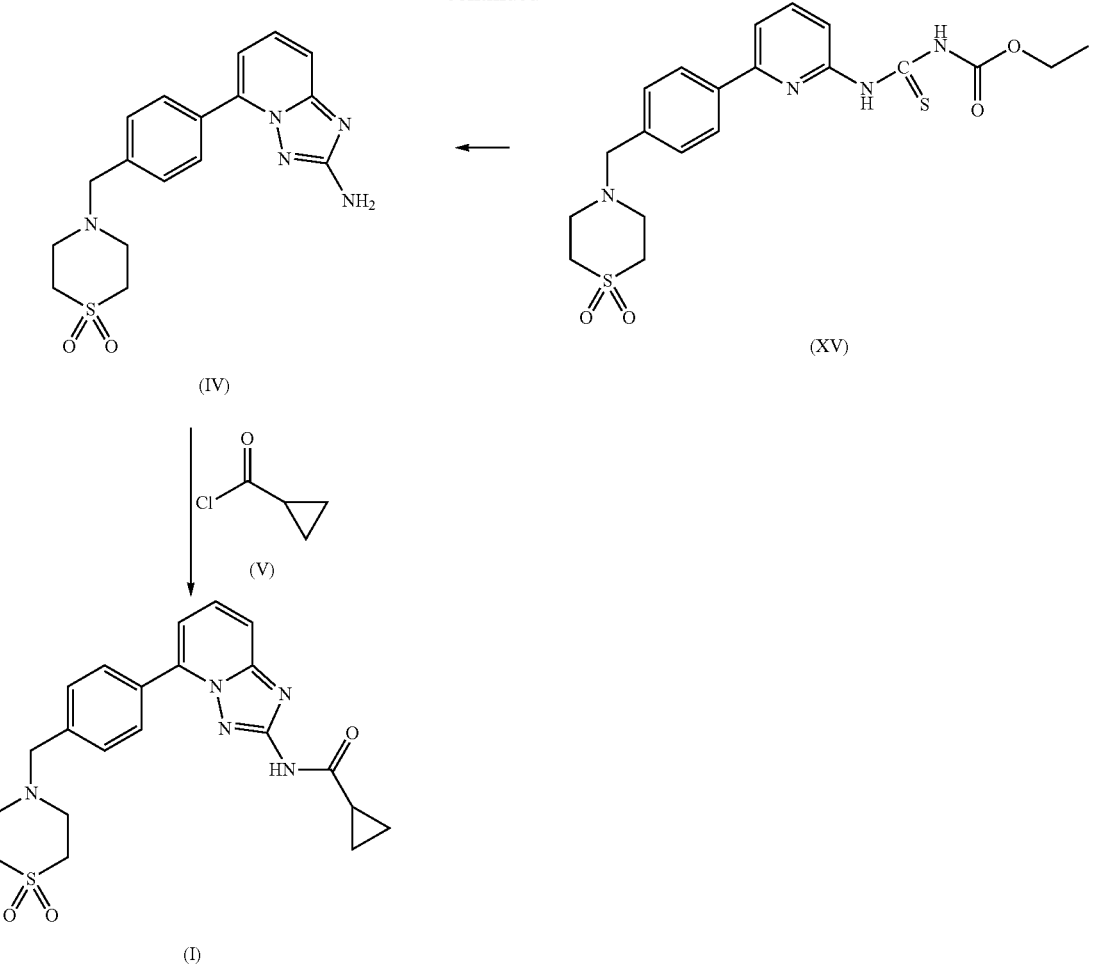

The present invention is further illustrated by the following examples which are provided merely to exemplify the invention and do not limit the scope of it.

EXAMPLES

Example-1: Preparation of Compound of Compound of Formula (IV)

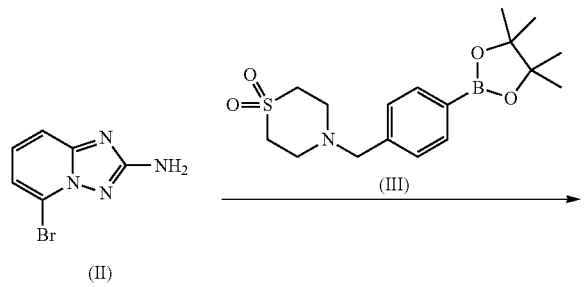

-continued 4-(4-(4,4,5,5-tetramethyl-1,3,2-dioxoborolan-2-yl)benzyl)thiomorpholine 1,1-dioxide (2 eq) of Formula (III) was added to a solution of 5-Bromo-[1,2,4]Triazolo[1,5-a]pyridine-2-ylamine of Formula (II) in 1,4-dioxane/water (5:1). Cesium carbonate $Cs_2CO_3$ (2 eq.) and $PdCl_2dppf$ (0.05%) was added to above solution. The resulting mixture was then heated in at 85-90° C. Water was added and to obtain 4-(4-(2-amino-[1,2,4]triazolo[1,5-a]pyridin-5-yl)benzyl)thiomorpholine1,1-dioxide compound of Formula (IV).

Example-2: Preparation of Filgotinib

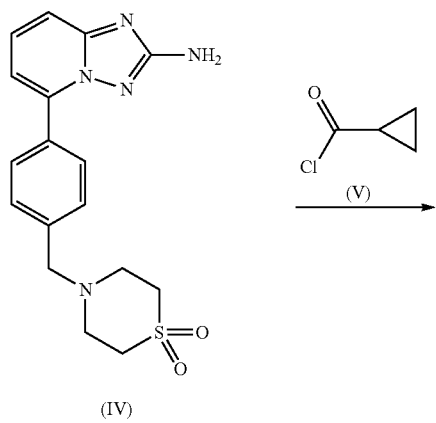

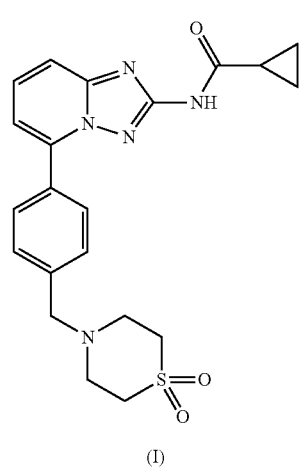

4-(4-(2-amino-[1,2,4]triazolo[1,5-a]pyridin-5-yl)benzyl) thiomorpholine-1,1-dioxide compound of Formula (IV) (10.83 g 33.3 mmol.) in MDC (150 ml) at 5° C., was added triethylamine (11.6 ml, 83.3 mmol) followed by cyclopropanecarbonyl chloride of Formula (V) (83.3 mmol). The reaction mixture was then allowed to warm to ambient temperature and stirred until all starting material was consumed. If required, further Triethyl amine (4.64 ml, 33.3 mmol) and cyclopropanecarbonyl chloride of Formula (V) (33.3 mmol) was added to ensure complete reaction. After standard work up procedure solvent was evaporated and crude solid was purified in mixture of dimethyl acetamide-toluene. Further after purification resulted solid was treated with aqueous ammonia solution (50 ml) and stirred at ambient temperature to hydrolyze any bis-acylated product. Product was obtained filtration. Further crude Filgotinib was purified in acetone (50 ml). The solid was collected by filtration, washed with acetone (50 ml) and dried in vacuum to give pure filgotinib.

Example-3: Preparation of Compound of Formula (VIII)

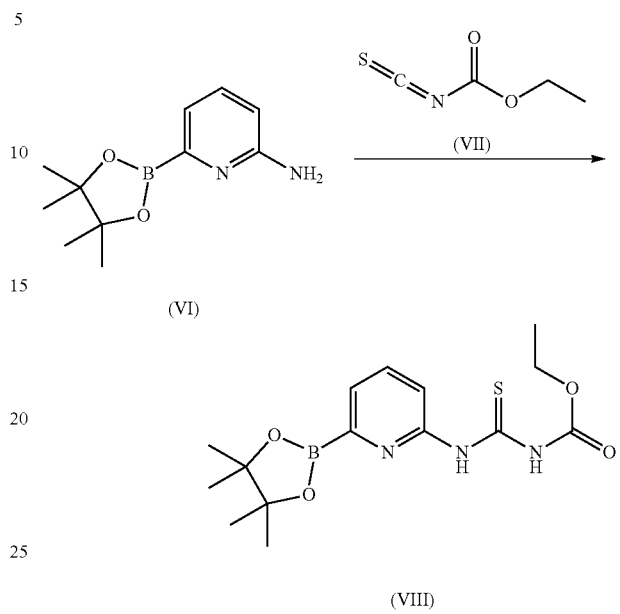

Cooled solution of 6-(4,4,5,5-tetramethyl-1,3,2-dioxaborolan-2-yl)pyridine-2-amine of Formula (VI) (322.74 g, 1.467 mol.) was added in MDC at 5° C. To the above cooled solution was added ethoxycarbonylisothiocyanate of Formula (VII) (173 ml) drop wise. The reaction mixture then allowed to warm to room temperature and stirred till reaction complies. Solvent was distilled out by evaporation under vacuum. Solid was slurred in heptane. Finally product was isolated by filtration followed by washing with n-Heptane.

Example-4: Preparation of Compound of Formula (IX)

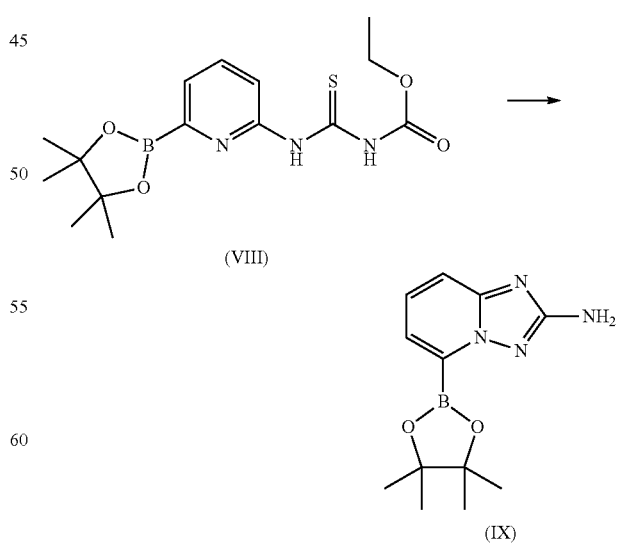

N,N-diisopropylethylamine (145.3 ml) was added to a suspension of hydroxyl amine hydrochloride (101.8 g) in ethanol/methanol (1:1,900 ml) and the mixture was stirred at room temperature for 1 to 3 hours. Compound of Formula (VIII) (102.9 g, 0.293 mol) was then added and the mixture was slowly heated to reflux temperature. After 3 h at reflux, the mixture was allowed to cool and filtered to collect to the precipitated solid. Further product was collected by evaporation of filtrate ML under vacuum followed by addition of water (250 ml) and filtration. The combined solids was washed successively with water (250 ml), ethanol/methanol (1:1,250 ml) and ethyl acetate (250 ml) then dried in vacuum to afford 5-(4,4,5,5-tetramethyl-1,3,2-dioxaborolan-2-yl)-[Triazolo[1,5-a]pyridine-2-amine] compound of Formula (IX) as a solid.

Example-5: Preparation of Compound of Formula (X)

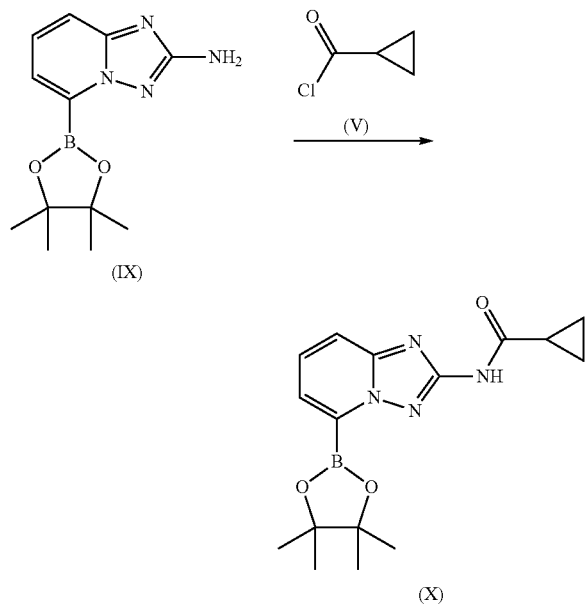

To a solution of the 5-(4,4,5,5-tetramethyl-1,3,2-dioxaborolan-2-yl)-[Triazolo[1,5-a]pyridine-2-amine] compound of Formula (IX) (10.83 g 33.3 mmol.) in dry acetonitrile (150 ml) at 5° C. was added triethylamine (11.6 ml, 83.3 mmol) followed by cyclopropane carbonyl chloride of Formula (V) (83.3 mmol). The reaction mixture was then allowed to warm to ambient temperature and stirred until all starting material was consumed. If required, further Triethyl amine (4.64 ml, 33.3 mmol) and cyclopropane carbonyl chloride of Formula (V) (33.3 mmol) was added to ensure complete reaction. After reaction complies solvent was evaporated and resulted solid was treated with Methanolic ammonia solution (50 ml) and stirred at ambient temperature to hydrolyze any bis-acylated product. Product isolation was carried out by removal of volatiles solvent followed by trituration with diisopropyl ether (50 ml). The solids was collected by filtration, washed with water (100 ml), acetone (50 ml) and diisopropyl ether (50 ml), then dried in vacuum to give the N-5-(4,4,5,5-tetramethyl-1,3,2-dioxaborolan-2-yl)-[1,2,4]Triazolo[1,5-a]pyridine-2-yl]cyclopropanecarboxamide of Formula (X).

Example-6: Preparation of Filgotinib

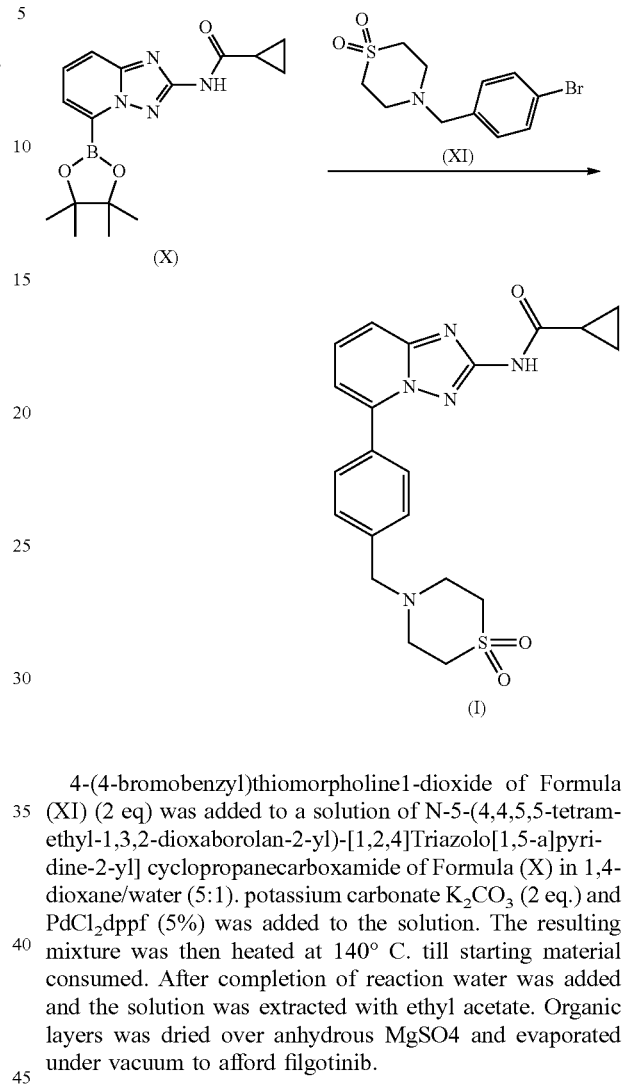

4-(4-bromobenzyl)thiomorpholine1-dioxide of Formula (XI) (2 eq) was added to a solution of N-5-(4,4,5,5-tetramethyl-1,3,2-dioxaborolan-2-yl)-[1,2,4]Triazolo[1,5-a]pyridine-2-yl] cyclopropanecarboxamide of Formula (X) in 1,4-dioxane/water (5:1). potassium carbonate $K_2CO_3$ (2 eq.) and $PdCl_2dppf$ (5%) was added to the solution. The resulting mixture was then heated at 140° C. till starting material consumed. After completion of reaction water was added and the solution was extracted with ethyl acetate. Organic layers was dried over anhydrous MgSO4 and evaporated under vacuum to afford filgotinib.

Example-7: Preparation of Compound of Formula (XIII)

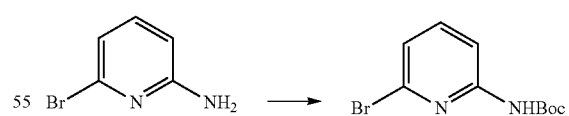

Di-tert-butyldicarbonate (Boc anhydride) (2 eq) was added to a solution of 6-bromopyridine-2-amine of Formula (XII) and triethyl amine (2 M. eq.) in MDC (5 vol.). The resulting mixture was then stirred at ambient temperature. After reaction complies water was added and the product was extracted with organic layer. The organic layers were dried over anhydrous MgSO4 and evaporated under vacuum to give compound of Formula (XIII).

Example-8: Preparation of Compound of Formula (III)

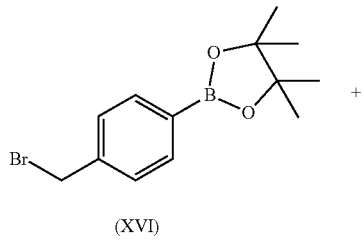

(XVI)

+

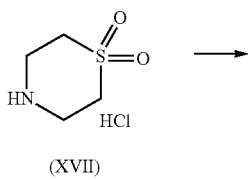

(XVII)

→

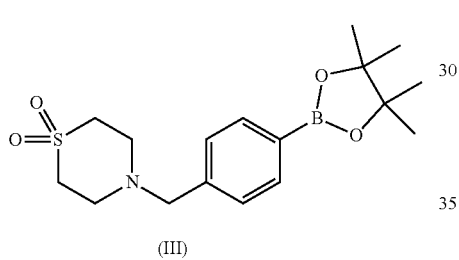

(III)

2-(4-(bromomethyl)phenyl)-4,4,5,5-tetramethyl-1,3,2-dioxaborolane of Formula (XVI) (80 g) was added in acetone (500 ml) followed by addition of potassium carbonate (130 g) at 25° C. to 35° C. Further, thiomorpholine 1,1-dioxide hydrochloride of Formula (XVII) was added and reaction was heated at 50° C. to 55° C. and maintained for 5 hours. Acetone was distilled and reaction mass was cooled to 25° C. to 35° C., followed by addition of water (500 ml) and stirred for 60 minutes. The reaction mass was filtered and washed with water (2×100 ml) to obtain compound of Formula (III) (100 g).

Example-9: Preparation of Compound of Formula (XIV)

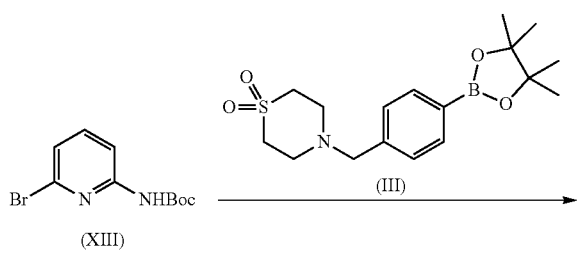

(XIII)

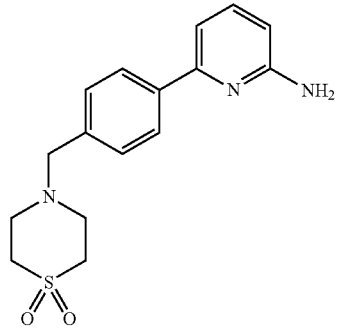

(XIV)

4-(4-(4,4,5,5-tetramethyl-1,3,2-dioxoborolan-2-yl)benzyl)thiomorpholine1,1-dioxide (2 eq) of Formula (III) was added to a solution of tert-butyl (6-bromopyridin-2-yl) carbamate of Formula (XIII) in 1,4-dioxane/water (5:1). Potassium carbonate K$_2$CO$_3$ (2 eq.) and PdCl2dppf (5%) were added to above solution. The resulting mixture was then heated in at 100° C. Water was added and the solution was extracted with ethyl acetate to obtain compound of Formula (XV).

Example-10: Preparation of Compound of Formula (XIV)

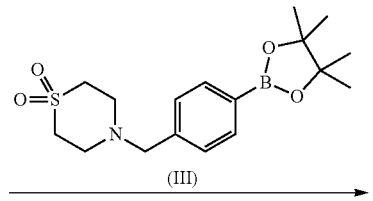

(XII)

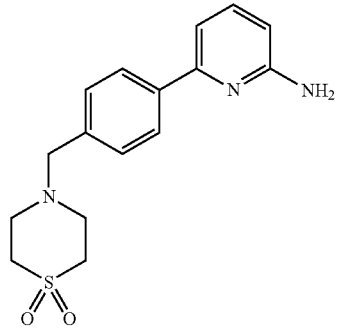

(XIV)

6-Bromopyridine-2-amine of Formula (XII) (50 g) and 4-(4-(4,4,5,5-tetramethyl-1,3,2-dioxoborolan-2-yl)benzyl) thiomorpholine1,1-dioxide of Formula (III) (100 g) and 1,4-dioxane (700 ml) were added at 25° C. to 35° C. Cesium carbonate (150 g), water (300 ml) and tetrakis(triphenylphosphine) palladium(0) (9 g) were added and reaction mass was heated to 85° C. to 90° C. and maintained for 7 hours. The reaction mass was cooled to 25° C. to 35° C. and settled and for 15 minutes. Layers were separated and to the filtrate ML, water (400 ml) was added and stirred for 2 hours. The reaction mass was filtered and washed with water (2×50 ml) to obtain compound of Formula (XIV), which was further purified by Dimethyl acetamide (1 vol) and toluene (7 vol) to obtain compound of Formula (XIV) (50 g).

Example-11: Preparation of Compound of Formula (XV)

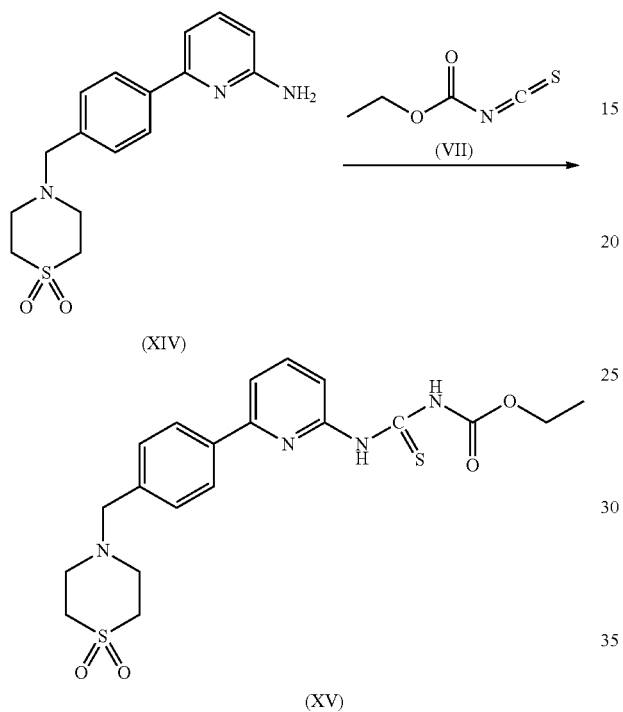

Cooled solution of compound of Formula (XIV) (322.74 g, 1.467 mol.) was added in MDC at 5° C. To the above cooled solution was added ethoxycarbonyl isothiocyanate of Formula (VII) (173 ml) drop wise. The reaction mixture then allowed to warm to room temperature and stirred till reaction complies. Solvent was distilled out by evaporation under vacuum. Solid was slurred in methanol. Finally product was isolated by filtration followed by washing with methanol.

Example-12: Preparation of Compound of Formula (IV)

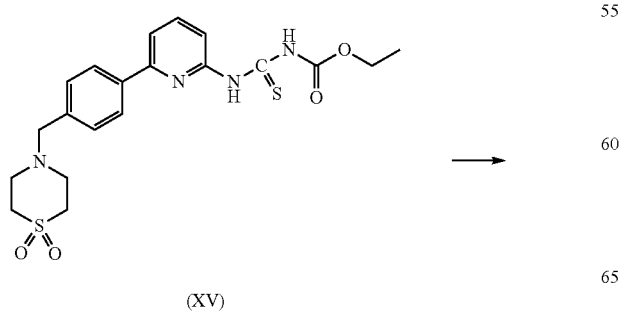

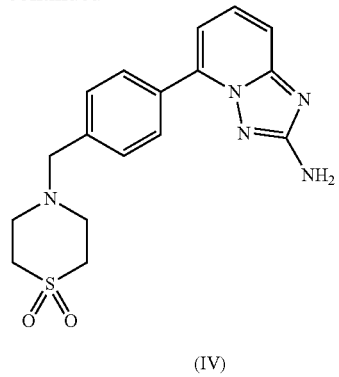

N,N-diisopropylethylamine (145.3 ml) was added to a suspension of hydroxyl amine hydrochloride (101.8 g) in methanol (1:1,900 ml) and the mixture was stirred at room temperature for 1 to 3 hours. Compound of Formula (XV) (102.9 g, 0.293 mol) was then added and the mixture was slowly heated to reflux temperature. After 5 hours at reflux, the mixture was allowed to cool and filtered to collect to the precipitated solid. Further product was purified in acetone solvent. Finally product was dried in vacuum to afford compound of Formula (IV) as a solid.

While the present invention has been described in terms of its specific embodiments, certain modifications and equivalents will be apparent to those skilled in the art and are intended to be included within the scope of the present invention.

We claim:
1. A process for the preparation of filgotinib of Formula (I),

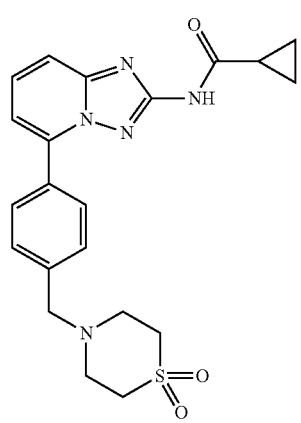

comprising the steps of:
(a) reacting a compound of Formula (XII) with a compound of Formula (III) using a catalyst in the presence of a base in one or more solvents to obtain a compound of Formula (XIV);

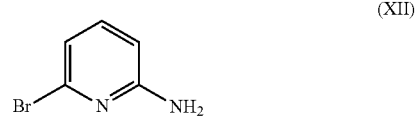

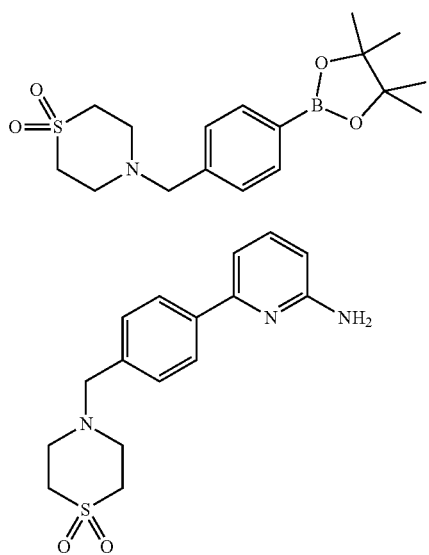

(b) reacting the compound of Formula (XIV) with ethoxy-carbonyl isothiocynate of Formula (VII) in one or more solvents to obtain a compound of Formula (XV);

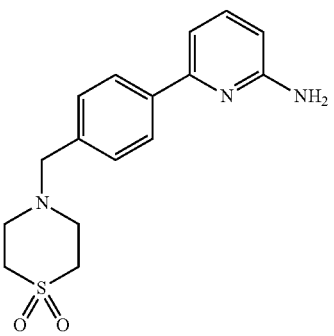

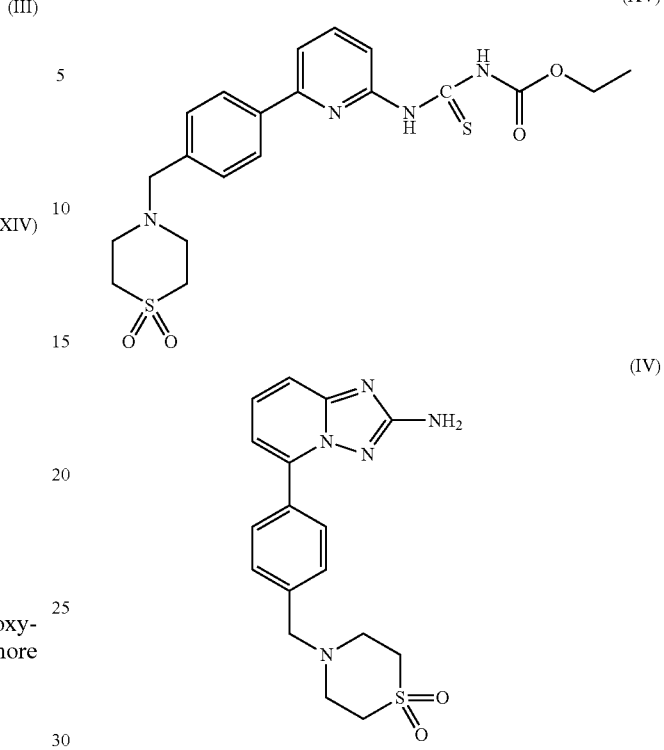

(c) reacting the compound of Formula (XV) with a base in the presence of one or more solvents to obtain a compound of Formula (IV); and (d) reacting the compound of Formula (IV) with cyclopropane carbonyl chloride of Formula (V) in the presence of a base and one or more solvents to obtain filgotinib of Formula (I).

2. The process according to claim 1, wherein the catalyst is selected from Palladium scavenger, Pd(PPh$_3$)$_4$, PdCl$_2$(PPh$_3$)$_4$, PdCl$_2$(dppf) and PdCl$_2$(dppe).

3. The process according to claim 1, wherein the base is selected from an organic or inorganic base.

4. The process according to claim 3, wherein the base is selected from diisopropylethylamine, diisopropylamine, triethylamine, diethylamine, piperidine, morpholine, pyridine, DBU, DABCO, sodium hydroxide, potassium hydroxide, lithium hydroxide, sodium carbonate, potassium carbonate and cesium carbonate.

5. The process according to claim 1, wherein the solvent comprises one or more of C$_{1-4}$ alcohols, C$_{2-6}$ esters, C$_{2-6}$ ketones, halogenated hydrocarbons, polar aprotic solvents, tetrahydrofuran, 2-methyltetrahydrofuran, dioxane, or mixtures thereof.

6. The process according to claim 5, wherein the solvent is selected from methanol, ethanol, n-propanol, isopropanol, n-butanol; ethyl acetate, propyl acetate, isopropyl acetate, t-butyl acetate, and isobutyl acetate; acetone, methyl ethyl ketone, and methyl isobutyl ketone; methylene dichloride, ethylene dichloride, carbon tetrachloride, chlorobenzene; dimethylformamide, dimethylsulfoxide, dioxane and N-methylpyrrolidone, or mixtures thereof.

7. A process for the preparation of filgotinib comprising the steps of:

(a) reacting a compound of Formula (II) with a compound of Formula (III) using a catalyst in the presence of a base and one or more solvents to obtain a compound of Formula (IV); and (II)

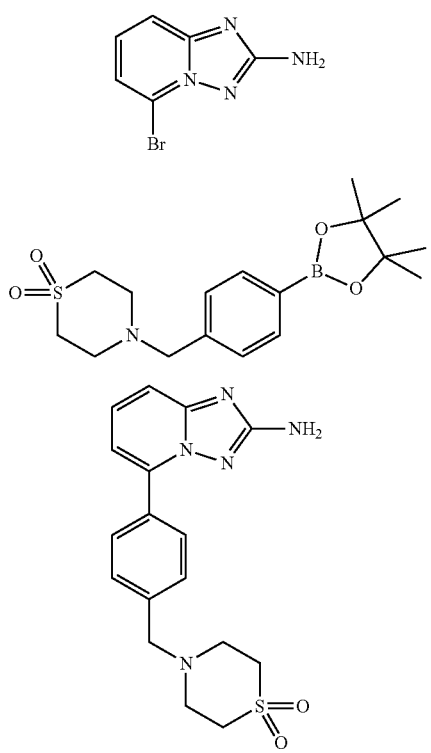

(III)

(IV)

(b) reacting the compound of Formula (IV) with cyclopropanecarbonyl chloride of Formula (V) in the presence of a base and one or more solvents to obtain filgotinib (IV)

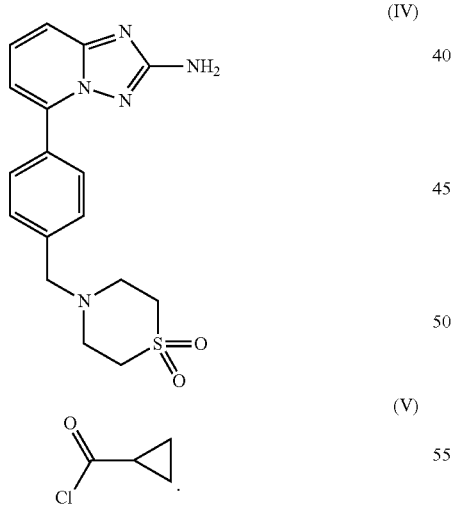

(V)

8. The process according to claim 7, wherein the catalyst is selected from Palladium scavenger, Pd(PPh$_3$)$_4$, PdCl$_2$(PPh$_3$)$_4$, PdCl$_2$(dppf) and PdCl$_2$(dppe).

9. The process according to claim 7, wherein the base is selected from diisopropylethylamine, diisopropylamine, triethylamine, diethylamine, piperidine, morpholine, pyridine, DBU, DABCO, sodium hydroxide, potassium hydroxide, lithium hydroxide, sodium carbonate, potassium carbonate and cesium carbonate.

10. The process of according to claim 7, wherein the solvent comprises one or more of C$_{1-4}$ alcohols, C$_{2-6}$ esters, C$_{2-6}$ ketones, halogenated hydrocarbons, polar aprotic solvents, tetrahydrofuran, 2-methyltetrahydrofuran, dioxane, or mixtures thereof.

11. A process for the preparation of filgotinib comprising the steps of:

(a) reacting a compound of Formula (VI) with ethoxycarbonyl isothiocynate of Formula (VII) to obtain a compound of Formula (VIII);

(VI)

(VII)

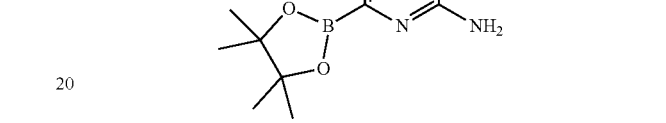

(VIII)

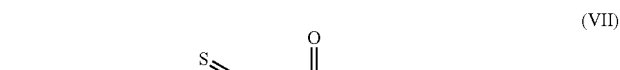

(b) converting the compound of Formula (VIII) to a compound of Formula (IX) in the presence of a base and one or more solvents;

(VIII)

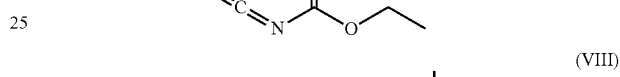

(IX)

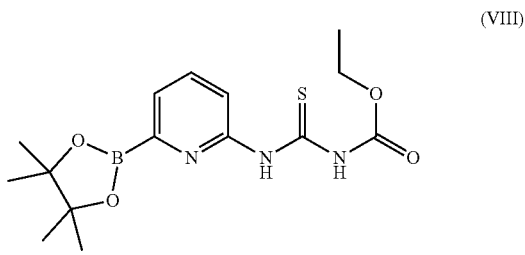 [SMILES: CCOC(=O)NC(=S)Nc1cccc(B2OC(C)(C)C(C)(C)O2)n1]

(c) reacting the compound of Formula (IX) with cyclopropane carbonyl chloride of Formula (V) in the presence of abase and one or more solvents to obtain a compound of Formula (X); and

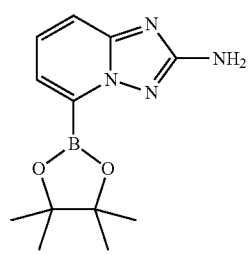

(IX)

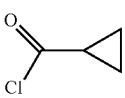

(V)

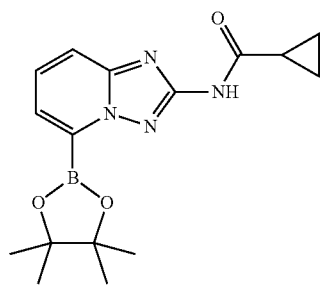

(X)

(d) reacting the compound of Formula (X) with 4-(4-bromobenzyl)thiomorpholine 1,1-dioxide of Formula (XI) using a catalyst in presence of a base and one or more solvents to obtain filgotinib.

12. The process according to claim 11, wherein the catalyst is selected from Palladium scavenger, Pd(PPh$_3$)$_4$, PdCl$_2$(PPh$_3$)$_4$, PdCl$_2$(dppf) and PdCl$_2$(dppe).

13. The process according to claim 11, wherein the base is selected from an organic or inorganic base.

14. The process according to claim 11, wherein the solvent comprises one or more of C$_{1-4}$ alcohols, C$_{2-6}$ esters, C$_{2-6}$ ketones, halogenated hydrocarbons, polar aprotic solvents, tetrahydrofuran, 2-methyltetrahydrofuran, dioxane, or mixtures thereof.

15. A compound of Formula (VIII)

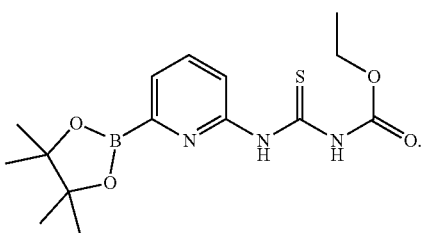

(VIII)

16. A compound of Form a (IX)

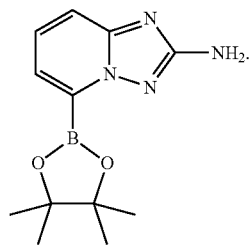

(IX)

17. A compound of Formula (X)

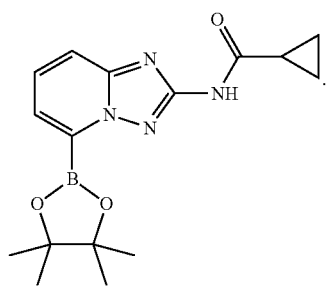

(X)

* * * * *